United States Patent
Jiang et al.

(10) Patent No.: US 10,168,212 B2
(45) Date of Patent: Jan. 1, 2019

(54) OPTICAL SPECTROSCOPIC MEASUREMENT SYSTEM

(71) Applicant: Thorlabs, Inc., Newton, NJ (US)

(72) Inventors: James Jiang, Hackettstown, NJ (US); Marshall Scott, Newton, NJ (US); Eric Geoffrion, Montreal (CA); Alex Cable, Newton, NJ (US)

(73) Assignee: THORLABS, INC., Newton, NJ (US)

( * ) Notice: Subject to any disclaimer, the term of this patent is extended or adjusted under 35 U.S.C. 154(b) by 308 days.

(21) Appl. No.: 14/964,956

(22) Filed: Dec. 10, 2015

(65) Prior Publication Data

US 2016/0169740 A1    Jun. 16, 2016

Related U.S. Application Data (60) Provisional application No. 62/090,944, filed on Dec. 12, 2014.

(51) Int. Cl.
*G01J 3/36* (2006.01)
*G01J 3/433* (2006.01)
(Continued)

(52) U.S. Cl.
CPC ............... *G01J 3/36* (2013.01); *G01J 3/433* (2013.01); *G01J 3/4338* (2013.01);
(Continued)

(58) Field of Classification Search
CPC ......... G01J 3/36; G01J 3/433; G01N 21/1702
See application file for complete search history.

(56) References Cited

U.S. PATENT DOCUMENTS 5,002,060 A  *  3/1991  Nedivi .................. A61B 5/0205
                                                       310/329
5,127,267 A  *  7/1992  Huebler .................... G01S 5/22
                                                       73/40.5 A (Continued)

FOREIGN PATENT DOCUMENTS

| EP | 1990629 A1 | 11/2008 |
|---|---|---|
| RU | 77441 U1 | 10/2008 |
| WO | 2010106064 A1 | 9/2010 |

OTHER PUBLICATIONS

International Search Report with Written Opinion, dated Apr. 14, 2016, for corresponding international application PCT/US2015/064965.

(Continued)

*Primary Examiner* — Maurice Smith
(74) *Attorney, Agent, or Firm* — Myers Wolin, LLC (57) ABSTRACT

A system capable of highly sensitive measurement of material concentration values in a sample using an optical spectroscopic method is disclosed. The system utilizes high-speed data acquisition and high resolution sampling of the raw signals output by the sensors with reduced total channel counts, and performs frequency analysis of the signals using the Fourier transform method to process all sensor channels in parallel. When each sensor is targeting the detection of some certain materials at some certain frequencies, the system is capable of simultaneous detection of multiple materials of interest in the sample with high measurement sensitivity and high speed.

15 Claims, 9 Drawing Sheets

(51) Int. Cl.
G01N 21/17 (2006.01)
G01N 21/39 (2006.01)
(52) U.S. Cl.
CPC ......... G01N 21/1702 (2013.01); G01N 21/39 (2013.01); G01N 2201/0691 (2013.01); G01N 2201/06113 (2013.01); G01N 2201/12 (2013.01)

(56) References Cited

U.S. PATENT DOCUMENTS

| | | | | |
|---|---|---|---|---|
| 5,381,473 | A * | 1/1995 | Andrea | H04M 1/05 379/388.03 |
| 6,332,868 | B1 * | 12/2001 | Sato | A61B 5/0059 600/306 |
| 8,561,454 | B2 | 10/2013 | Muehleisen | |
| 2003/0205682 | A1 | 11/2003 | Kapoor et al. | |
| 2008/0277586 | A1 * | 11/2008 | Cardinale | G01M 3/002 250/339.13 |
| 2009/0303476 | A1 * | 12/2009 | Kosterev | G01N 21/1702 356/323 |
| 2010/0242572 | A1 * | 9/2010 | Yu | G01N 21/1702 73/24.02 |
| 2012/0250881 | A1 * | 10/2012 | Mulligan | H03F 1/0261 381/92 |

OTHER PUBLICATIONS

Lei Dong et al., "Compact Portable QEPAS Multi-gas Sensor", Quantum Sensing and Nanophotonic Devices VIII, Proceedings. of Spie, T.7945, 79450R, 2011.

Partial Supplementary European Search Report and written opinion, dated May 24, 2018, issued by the European Patent Office for corresponding European application No. 15868087.6.

McNaghten E D et al: "Simultaneous detection of trace gases using multiplexed tunable diode lasers and a photoacoustic cell containing a cantilever microphone", Applied Physics B ; vol. 107, No. 3, May 26, 2012, pp. 861-871, XP035071874.

A. A. Kosterev, Yu. A. Bakhirkin, R. F. Curl, and F. K. Tittel, "Quartz-enhanced photoacoustic spectroscopy," Optics Letters, vol. 27, No. 21, Nov. 1, 2002 (Nov. 1, 2002), p. 1902, XP055471369, ISSN: 0146-9592, DOI: 10.1364/OL.27.001902.

J. Chen et al:"Tunable diode laser spectroscopy with optimum wavelength scanning", Applied Physics B ; vol. 100, No. 2, Aug. 2010, pp. 331-339; https://doi.org/10.1007/s00340-010-3973-2.

Lei Dong, Anatoliy A. Kosterev, David Thomazy, Frank K. Tittel, "Compact portable QEPAS multi-gas sensor", Proc. SPIE 7945, Quantum Sensing and Nanophotonic Devices VIII, 79450R (Jan. 24, 2011); doi: 10.1117/12.875108; https://doi.org/10.1117/12.875108.

Alan Fried, Bruce Henry, and James R. Drummond, "Tunable diode laser ratio measurements of atmospheric constituents by employing dual fitting analysis and jump scanning," Applied Optics, vol. 32, Issue 6, pp. 821-827 (1993), https://doi.org/10.1364/AO.32.000821.

Supplementary European Search Report and written opinion, dated Jun. 29, 2018, issued by the European Patent Office for corresponding European application No. 15868087.6.

International Preliminary Report on Patentability (IPRP), dated Jun. 13, 2017 for corresponding International Application No. PCT/US2015/064965.

* cited by examiner

*FIG. 1*

(Prior Art)

FIG. 2

(Prior Art)

OPTICAL SPECTROSCOPIC MEASUREMENT SYSTEM

CROSS-REFERENCE TO RELATED APPLICATIONS

This application claims the benefit of U.S. Provisional Application No. 62/090,944 filed on Dec. 12, 2014, the contents of which are herein incorporated by reference.

FIELD OF THE INVENTION

The invention generally relates to optical spectroscopy systems. More particularly, the invention relates to an optical spectroscopy system for measuring material concentration values in a sample.

BACKGROUND

Optical instruments for highly sensitive gas sensing are being developed for use in future environmental, industrial, and health monitoring applications. To measure multiple sensor channels in an optical spectroscopic measurement system, the conventional methods either use multiple data acquisition channels, or use a time-multiplexing method to connect multiple sensor output to the same data acquisition channels. These solutions result in a higher total system cost due to an increased number of data acquisition channels or less efficient use of the output signal from a sensor due to dead measurement time.

Figure 1:
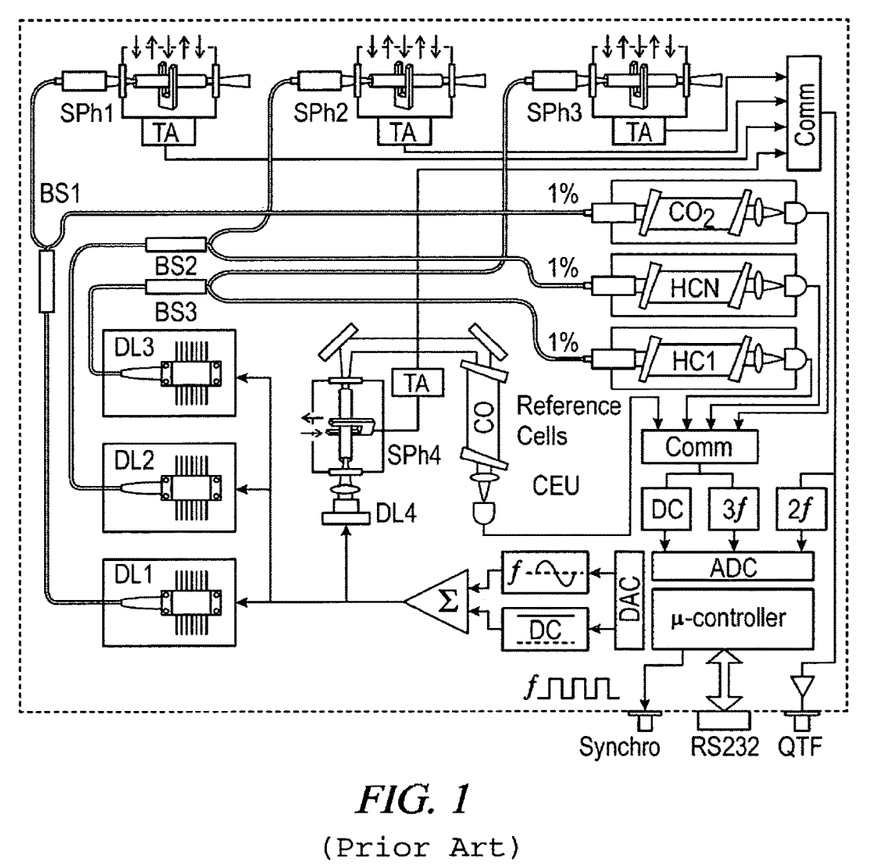
FIG. 1 illustrates an existing optical spectroscopic system for multiple gas components detection.

FIG. 1 is an illustration of an existing optical spectroscopic system for multiple gas components detection as disclosed by the publication "Compact Portable QEPAS Multi-gas Sensor", Proc. of SPIE Vol. 7945, 2011. When the laser is modulated by a sinusoidal waveform at a frequency of f, the material absorption signals in the sensor output are at the harmonic frequency of 2f, and the signal intensity at 2f is proportional to a material concentration value in the sample. The processed data is transferred to other devices (i.e., to another computer via the RS232 communication port) for display and storage. The system also provides a monitoring port of the 2f signal to the user.

As shown in FIG. 1, each sensor (a modified quartz tuning fork called spectrophone which is a piezoelectric element) is represented by SPh1 to SPh4. A trans-impedance amplifier (TA) is attached to each sensor to convert the tiny piezoelectric current signal generated by the sensor into a voltage signal to be digitized. The voltage signals from the four sensors are combined by a device (COMM) into one 2f signal. This signal combining device can be a voltage combiner or a signal switch.

Figure 2:
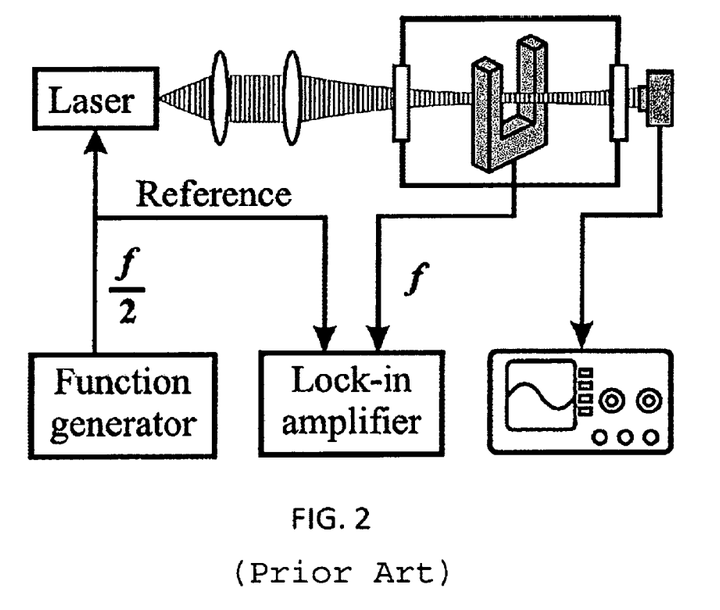
FIG. 2 illustrates an existing method that a lock-in amplifier is employed to measure the sensor signal intensity at the specified modulated frequency.

FIG. 2 shows that a lock-in amplifier is employed to measure the sensor signal intensity at the specified modulated frequency as disclosed by the publication: "Quartz-enhanced photoacoustic spectroscopy", Opt. Lett. V27, 1902, 2002. Because the lock-in amplifier is well-known for its capability of extracting a signal with a known carrier frequency from an extremely noisy environment, depending on the reference frequency supplied to the lock-in amplifier, the system is capable of detecting one modulation frequency for one sensor at a time. However, the total measurement time of the system is the sum of the measurement time of each sensor channel.

In optical spectroscopic measurement, when the light energy is absorbed by the targeted sample material, some portion of the absorbed energy is converted into other forms of energy such as light of different wavelengths, ultrasonic waves and heat energy radiated from the sample. A special sensor can be used to detect this radiated energy from the sample. In order for the sensor to effectively differentiate the energy radiated by the sample from other environmental noise, the excitation light is often intensity modulated or wavelength modulated in time, and the radiated energy from the sample has the same modulation frequency. Because the sensor is often designed to have one fundamental resonant frequency, it is important to choose the intensity modulation frequency of the light source to match the resonant frequency of the sensor to produce the maximum detection efficiency.

As shown in FIG. 1, a sinusoidal waveform is frequently used to modulate the intensity or the wavelength of the light source used in optical spectroscopic measurement. Because the energy conversion process in the sample is usually not a perfect linear process, the sample radiated energy will contain the fundamental modulation frequency and harmonic components. A sensor with only one resonant frequency can only response to one frequency excitation and has much weaker or no response at the harmonic frequencies. The sample radiated energy at the harmonics of the modulated frequency is not detectable by the sensor and become wasted.

As discussed above, the existing systems are very complex and inefficient. Therefore, there is a need to solve the challenges in highly sensitive material analysis using optical spectroscopic method which require increased sample measurement channels, reduced system complexity and improved measurement efficiency and detection sensitivity.

SUMMARY

One embodiment of the invention provides a system for measuring material concentration values in a sample, including: a plurality of laser sources modulated at different frequencies, each laser source emits light into the sample; a plurality of sensors to detect output signals from the sample; a signal combiner module to combine the output signals detected by the plurality of sensors into a combined signal; a data acquisition (DAQ) device to digitize the combined signal; a Fourier transform unit to perform a Fourier transform on the digitized signal to obtain signal intensity at each of the modulation frequencies in parallel; and a digital signal processor to calculate the material concentration values in the sample.

Another embodiment of the invention provides a method for measuring material concentration values in a sample, including: directing light from a plurality of laser sources modulated at different frequencies into the sample; detecting output signals from the sample with a plurality of sensors; combining and converting the output signals detected by the plurality of sensors into a voltage signal; digitizing the voltage signal; performing a Fourier transform on the digitized signal to obtain a signal intensity at each of the modulated frequencies in parallel; and calculating the material concentration values in the sample.

Another embodiment of the invention provides a method for compensating a drifting of a modulation center wavelength of a laser source, including: converting the drifting of the center wavelength into a pulsed signal, and the duty cycle of the pulsed signal is proportional to the drifting of the center wavelength; measuring the duty cycle of the pulsed signal to determine the drifting of the center wavelength; and generating a control signal for a current driver of the laser source to compensate the drifting.

Another embodiment of the invention provides a method for improving a detection sensitivity of an optical spectroscopy system, including: generating a modulation waveform connected to a driver of a laser source; transmitting a modulated light from the laser source through a reference cell and detecting a sample absorption curve of the reference cell; measuring a sample absorption frequency spectrum; measuring a sensor frequency response spectrum and identifying a sensor peak response frequency; and designing a customized modulation waveform to improve the signal intensity at the sensor peak response frequency, in the sample absorption frequency spectrum.

DETAILED DESCRIPTION OF THE PREFERRED EMBODIMENTS

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

This disclosure describes the best mode or modes of practicing the invention as presently contemplated. This description is not intended to be understood in a limiting sense, but provides an example of the invention presented solely for illustrative purposes by reference to the accompanying drawings to advise one of ordinary skill in the art of the advantages and construction of the invention. In the various views of the drawings, like reference characters designate like or similar parts.

The conventional spectroscopic analysis systems use discrete sensors each targeting one type of material to be detected, and each sensor has its own signal output channel connecting to the data acquisition (DAQ) devices. The system requires multiple DAQ channels or time-sharing of same DAQ channel for all the sensors.

This document discloses a system that utilizes one high-speed data acquisition channel to sample the output signals from multiple sensors, and followed by Fourier frequency analysis to process multiple sensor channels at the same time. The signals from multiple sensor channels in the new system are multiplexed in signal frequencies and can be digitized simultaneously and processed in parallel. Because of the totally reduced data acquisition and processing channels, the system is more efficient and the system can potentially achieve higher detection sensitivity than conventional systems.

Figure 3:
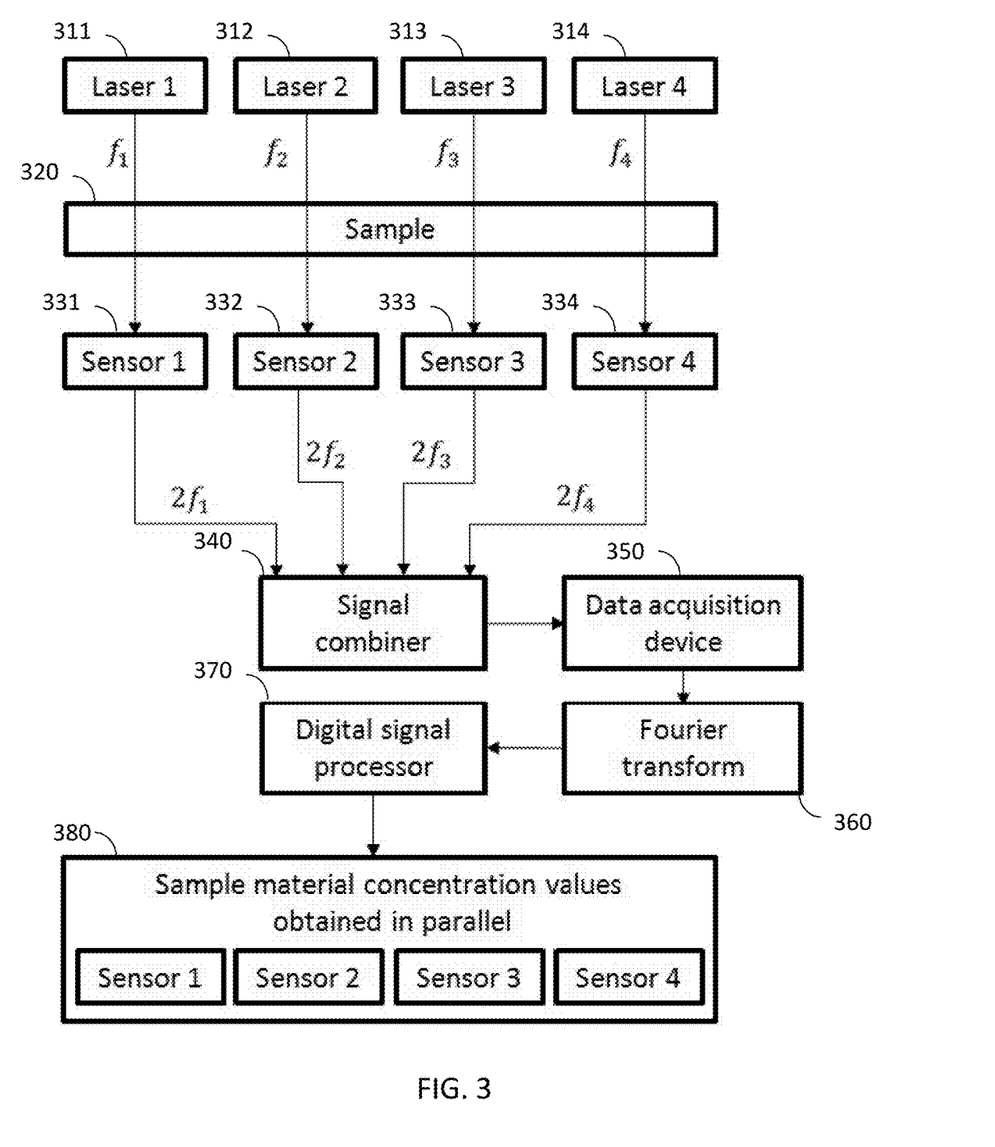
FIG. 3 illustrates an optical spectroscopic system for simultaneous measurement of multiple material components according to an embodiment.

FIG. 3 shows an optical spectroscopic system that is capable of simultaneous measurement of multiple material components in the same sample according to one embodiment. Multiple laser sources 311, 312, 313, 314 are modulated at different fundamental frequencies (f1 to f4) optimized for different sensors 331, 332, 333, 334. In one embodiment, the sensors have different resonant frequencies. In another embodiment, the sensors are based on the use of a quartz tuning fork (QTF) as a detector for acoustic oscillations induced in an absorbing gas by modulated optical radiation. Other types of optical spectroscopy sensors are contemplated. The output signal from each sensor is mainly at the second harmonic (2f1 to 2f4) of the excitation laser modulation frequency. Note that for clarity and without loss of generality, four laser sources and four sensors are shown in FIG. 3. It is understood that the disclosed system can accommodate a different number of laser sources and sensors including one single channel.

Different signal frequencies from different sensors are combined at the signal combiner 340 into a combined signal. In one embodiment, the signal combiner can be a transimpedance amplifier or a voltage adding circuit and the combined signal is a voltage signal. A high-speed data acquisition (DAQ) device 350 digitizes the combined signal at the sampling rate that is at least or higher than that required by the Nyquist sampling rate to improve the SNR (signal to noise ratio) of the measured signals. A processing unit 360 applies Fourier transform to the digitized signals to calculate the frequency spectrum of the combined signal. The signal intensity at different modulation frequencies are obtained in parallel in the Fourier transform process. A digital signal processor 370 performs necessary signal processing steps including filtering, averaging and background subtraction, to obtain the material concentration values as the measurement results 380. It is understood that the Fourier transform and the digital signal processing may be performed by one or more circuits, processors or subsystems configured with instructions or programming code to perform one or more such functions.

An embodiment includes following three aspects: (1) To combine the output signals from multiple sensors into one analog signal channel using a signal combiner. The combined signals in the one analog channel are digitized using one high-speed analog-to-digital conversion channel; (2) The sampling rate of the analog-to-digital conversion is equal or higher than required by the Nyquist sampling theory to capture the highest interested frequency signals; (3) A Fourier transform is applied to the digitized signals to calculate the signal intensities at all frequency components at the same time to separate the signals from different sensors; and (4) A digital signal processor calculates the sample material concentration values in all sensor channels in parallel.

A measurement method according to one embodiment employs a high speed DAQ card and Fourier transform for data acquisition and signal processing in spectroscopic measurement systems, and it can be applied to systems with one or multiple sensor channels. This method is an improvement over conventional systems using lock-in amplifiers for signal detection. In a method according to one embodiment, the raw signals from all sensor channels are frequency multiplexed into one signal path, captured with highest possible voltage resolution and time resolution during analog-to-digital conversion, and processed in parallel using Fourier transform. In contrast, the lock-in method uses a very narrow band-pass filter to detect the signal at the frequency of interest by rejecting all other frequency components. The signal detection efficiency is clearly higher with the method according to one embodiment.

In measuring the material concentration values in a sample with an optical spectroscopy system, the drifting of the modulation center wavelength of the laser source needs to be compensated.

Figure 4:
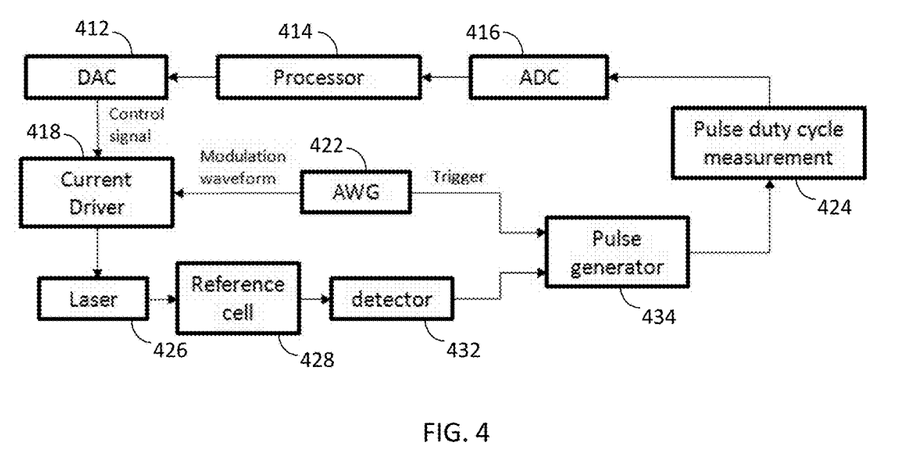
FIG. 4 illustrates an arrangement to compensate for the laser source modulation center wavelength drifting according to an embodiment.

FIG. 4 illustrates an embodiment designed to compensate for the modulation center wavelength drifting problem of the laser source for material absorption spectroscopic measurement. In one embodiment, the laser modulation center wavelength drifting is detected as a voltage signal for the processor to monitor and control to be constant. This goal is achieved in three steps: (1) convert the laser center wavelength drift into a pulsed signal, such that the duty cycle of the pulsed signal is proportional to the center wavelength drift; (2) measure the duty cycle of the pulsed signal 424 and convert it into a voltage signal which is detected by a processor 414 using an analog-to-digital converter (ADC) 416; (3) the processor outputs a control signal through a digital-to-analog converter (DAC) 412 to control the DC bias current output from the current controller 418 of the laser 426 to compensate for the drifting of wavelength.

As shown in FIG. 4, an arbitrary waveform generator (AWG) 422 provides the modulation waveform to the laser current driver 418 so that the laser output wavelength sweeps across the absorption wavelength of the material in the reference cell 428. The reference cell 428 contains a sample that absorbs the same wavelength as the sample to be detected by the system. The transmission of laser light through the reference cell 428 is then detected by a detector 432. The trigger output from the AWG is connected one input port of a pulse generator 434 and the detector output is connected to the other input port of the same pulse generator 434, the AWG trigger will set the pulse generator output to a high logic level at the beginning of the modulation cycle, and the absorption event in the optical detector output will set the pulse generator output to a low logic level. The rising edge and falling edge of the pulses are synchronized with the trigger event and wavelength absorbing event, respectively. Therefore the duty cycle of the pulse generator output stay in the high logic level is proportional to the time delay between the time when modulation trigger event occurs and the time when wavelength absorption event occurs. The changing of the duty cycle means the drifting of the modulation center wavelength of the laser source. A pulse duty cycle measurement module 424 measures the duty cycle of the pulsed signals coming out from the pulsed generator 434 as a voltage signal. In one embodiment the pulse duty cycle measurement module 424 uses a resistor-capacitor network.

Figure 5:
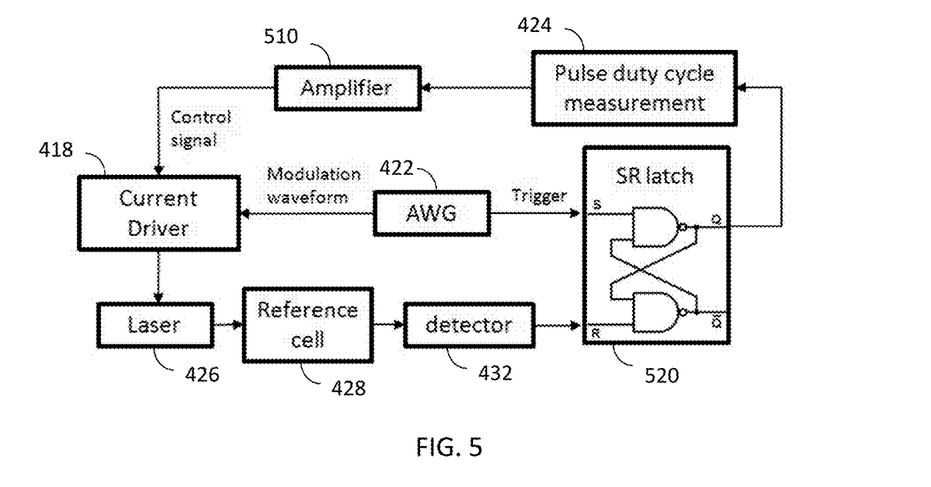
FIG. 5 illustrates an arrangement to compensate for the laser source modulation center wavelength drifting according to another embodiment.

Because the output of the pulse duty cycle measurement is a voltage signal, and the required DC bias control input of the current drive is also a voltage signal, a special amplifier 510, shown in FIG. 5, can be designed to replace the processor based control loop which requires one additional ADC 416 and DAC 412. FIG. 5 shows a circuit that can automatically compensate the modulation center wavelength drift of the laser source according to an embodiment. The processor 414, ADC 416 and DAC 412 shown in FIG. 4 are replaced by an amplifier 510. In one embodiment an "edge-triggered" set-reset (SR) latch 520 performs the function of the pulse generator 434.

Figure 6:
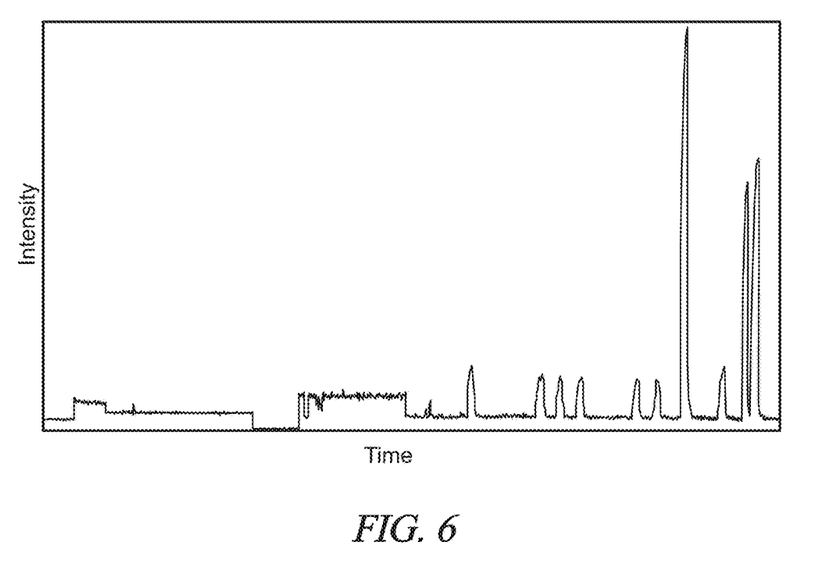
FIG. 6 shows a measurement result of CO concentration in human breath using a method according to an embodiment.

FIG. 6 shows the results of an experiment using the method according to an embodiment. As an example, this experiment measures CO level measurement in human breath from a few subjects, smoking and non-smoking. The results are calculated by software using the high-speed data acquisition followed by Fourier transform method. The signal intensity at the resonant frequency (32768 Hz) of the QTF gas sensor is proportional to the targeting gas (CO) concentration.

In the software display, the horizontal axis is time, and the vertical axis is the signal intensity proportional to the CO concentration in human breath. As shown in FIG. 6, in the right half of the display there are total 10 signal peaks that corresponds to 10 tests from multiple subjects. The time for each test is about 15 seconds.

In an optical spectroscopic system targeting the measurement of material concentration values in a sample, the light absorbed by the sample is radiated out in other types of energy, such as heat or ultrasonic waves, which are detectable by a sensor. The detection sensitivity of the system is highly dependent on the conversion efficiency between the radiated energy and the sensor.

Figure 7:
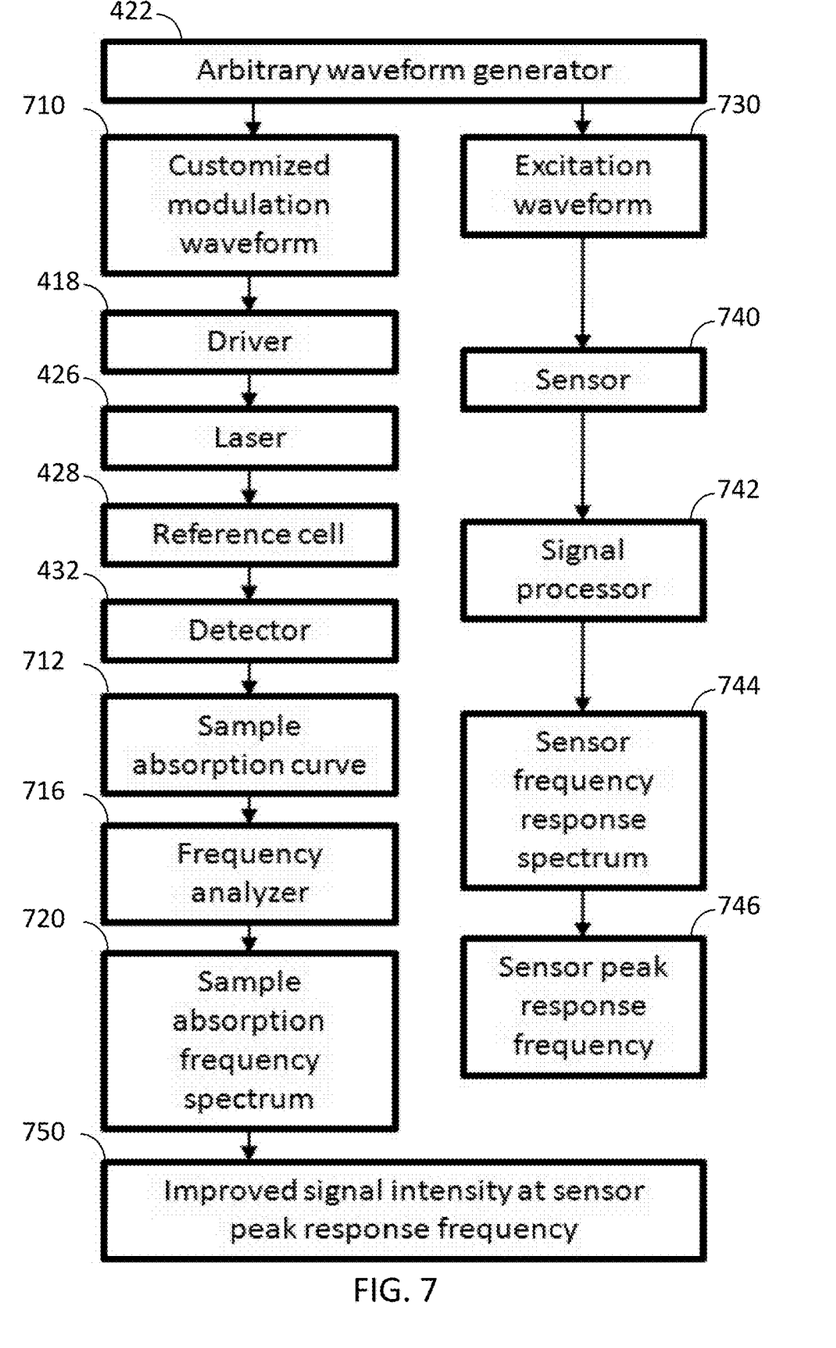
FIG. 7 shows a method to improve the measurement sensitivity of an optical spectroscopy system.

FIG. 7 shows one method to improve the detection sensitivity of an optical spectroscopy system: by designing a customized modulation waveform with improved signal intensity at the peak response frequency of the sensor, in the sample absorption frequency spectrum. This goal is achieved in following steps: (1) use an arbitrary waveform generator 422 to generate a customized modulation waveform 710 supplied to the driver 418 of the laser source 426, and transmit the modulated light through a reference cell 428 to a detector 432 to obtain the reference sample absorption curve 712; (2) use a frequency analyzer 716 to perform frequency analysis of the reference sample absorption curve 712 to obtain the sample absorption frequency spectrum 720. (3) use a waveform generator 422 to generate the excitation waveform 730 connected to the sensor 740, and measure the sensor frequency response spectrum 744 using a signal processor 742, and identify the sensor peak response frequency 746; (4) design the customized modulation waveform 710 so that the signal intensity at the sensor peak response frequency 746, in the sample absorption frequency spectrum 720, is improved. This method has the effect of slowing down the wavelength scanning speed of the laser source when the output wavelength is very close to the absorption wavelength of the sample, and allowing longer interaction time between the sample and the laser when the laser output wavelength is in the sample's absorbing wavelength window to increase the detected signal intensity output from the sensor.

Figure 8:
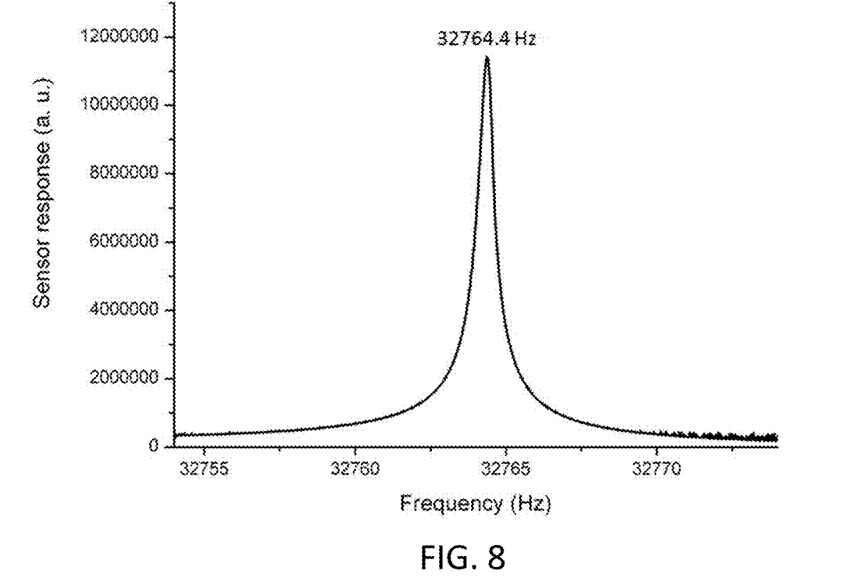
FIG. 8 shows the measured frequency response curve of a sensor within 10 Hz range near its resonant frequency of 32764.4 Hz.
Figure 9:
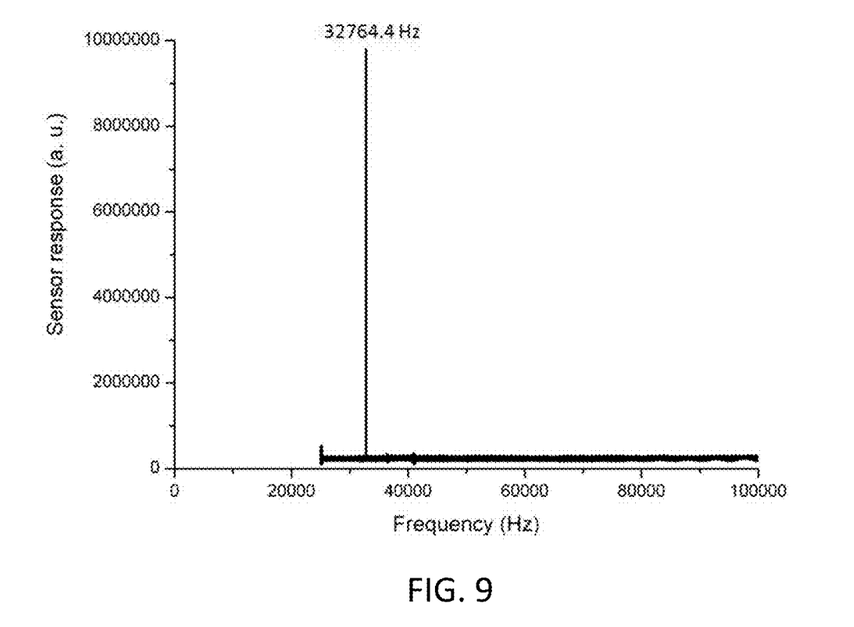
FIG. 9 shows the measured frequency response curve of the same sensor as in FIG. 7 but over a larger frequency range from 25 kHz to 100 kHz.

FIG. 8 shows the measured frequency response spectrum of a quartz tuning fork sensor within 10 Hz range near its fundamental resonant frequency of 32764.4 Hz. It is obtained by scanning the frequency of the excitation waveform from a waveform generator over the testing frequency range, and measure the sensor output signal intensity as a function of excitation frequency. This frequency response curve means that the sensor is much more sensitive to any environmental perturbations, such as ultrasonic vibrations or electric current stimulations, occurring at 32764.4 Hz than at other frequencies. FIG. 9 shows the measured frequency response spectrum of the same sensor over the frequency range from 25 kHz to 100 kHz. FIG. 9 shows that the sensor has only one resonant peak at the fundamental frequency of 32764.4 Hz, but no visible resonant peaks at second harmonic frequency of 65528.8 Hz and third harmonic frequency of 98293.2 Hz. Therefore, 32764.4 Hz is identified as the peak response frequency of the sensor.

Figure 10:
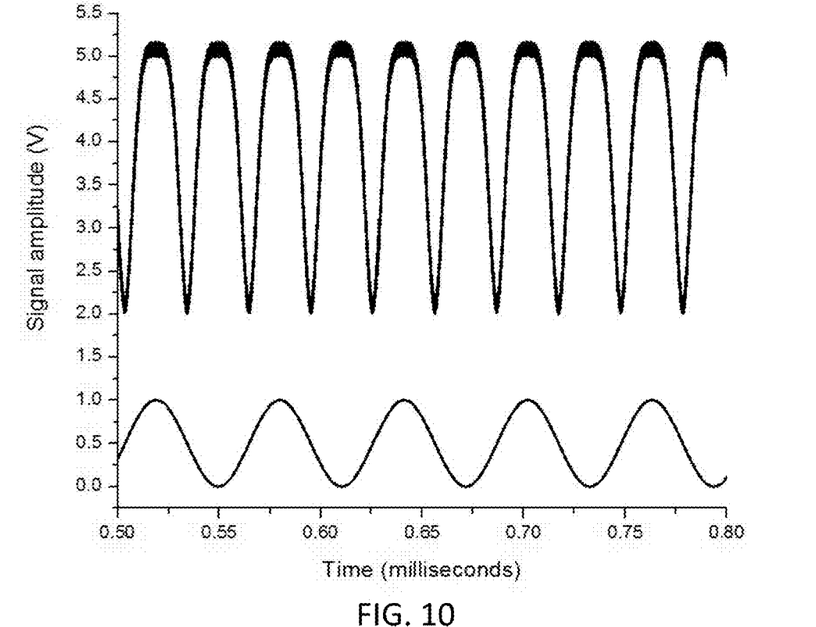
FIG. 10 shows the typical time trace of the sample absorption curve when the laser source is modulated by a sinusoidal waveform.

FIG. 10 shows two signals that can be measured on an oscilloscope. The top signal is the typical sample absorption curve showing the optical power change after the light passing through the sample contained in a reference cell. The bottom signal is the modulation waveform supplied to the current driver of the laser source. This signal is typically a sinusoidal waveform. The output optical power and wavelength of the laser source are modulated by this waveform. When the laser source is modulated at the frequency of f=16382.2 Hz, the absorption peaks appear at 2f=32784.4 Hz. This is because for every modulation cycle the laser output wavelength scans across the sample absorption line twice, one forward and one backward.

Figure 11:
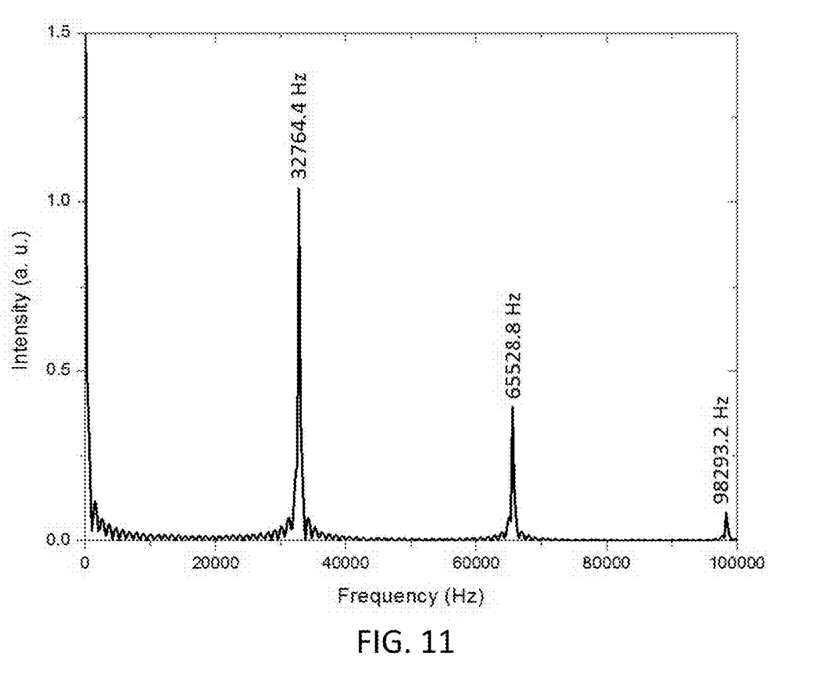
FIG. 11 shows the Fourier transform of the sample absorption curve in FIG. 9 to reveal its frequency components.

FIG. 11 shows the frequency components of the sample absorption curve in FIG. 9, after a Fourier transform of the signal. It shows that the sample absorption curve contains multiple frequency components: at the fundamental frequency of 32764.4 Hz, at the second harmonic frequency of 65528.8 Hz, and at the third harmonic frequency of 98293.2 Hz. This means that when the laser source is modulated by a sinusoidal waveform, the energy radiated out from the sample for detection has both fundamental and harmonic components. If a sensor with only fundamental resonant frequency as shown in FIG. 7 is used as the detector for the sample radiated energy, only the energy at the fundamental frequency can resonant with the sensor and is detected; the sample radiated energy at the harmonic frequencies cannot be detected by the sensor and is wasted.

Figure 12:
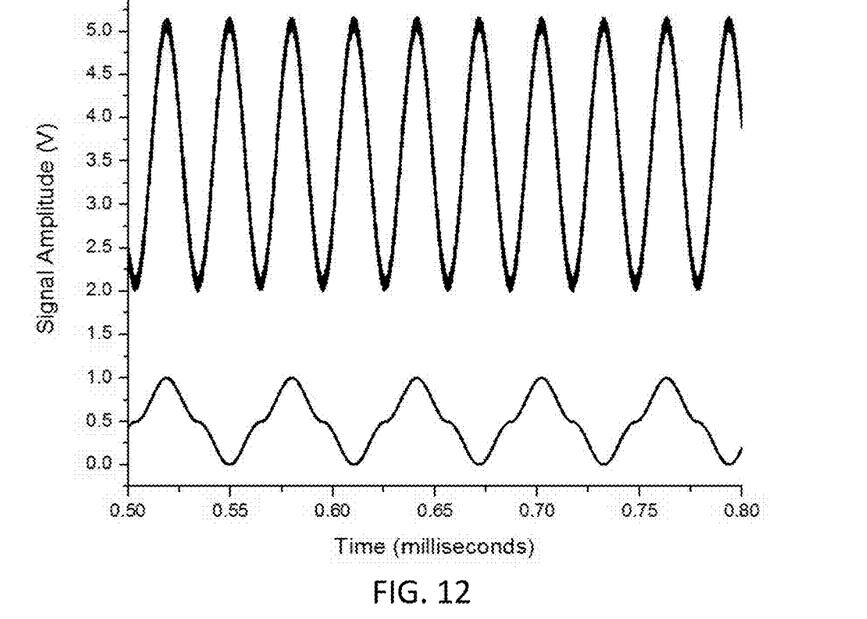
FIG. 12 shows the time trace of the optimized sample absorption curve when the laser source is modulated by a customized drive waveform.

FIG. 12 shows two signals measured using a similar method as FIG. 10. The top signal is an optimized sample absorption curve showing the optical power change after the light passing through the sample contained in a reference cell. The bottom signal is the customized drive waveform supplied to the current driver of the laser source which is not a sinusoidal waveform. This signal is customized to alter the wavelength scanning speed of the laser near the absorption wavelength of the sample, with the goal to convert the sample absorption curve into a sinusoidal shape optimized for the sensor. An important step to achieve this goal is by slowing down the wavelength scanning speed of the laser source when the output wavelength is very close to the absorption wavelength of the sample, essentially allowing longer interaction time between the sample and the laser when the laser output wavelength is in the sample's absorbing wavelength window.

Figure 13:
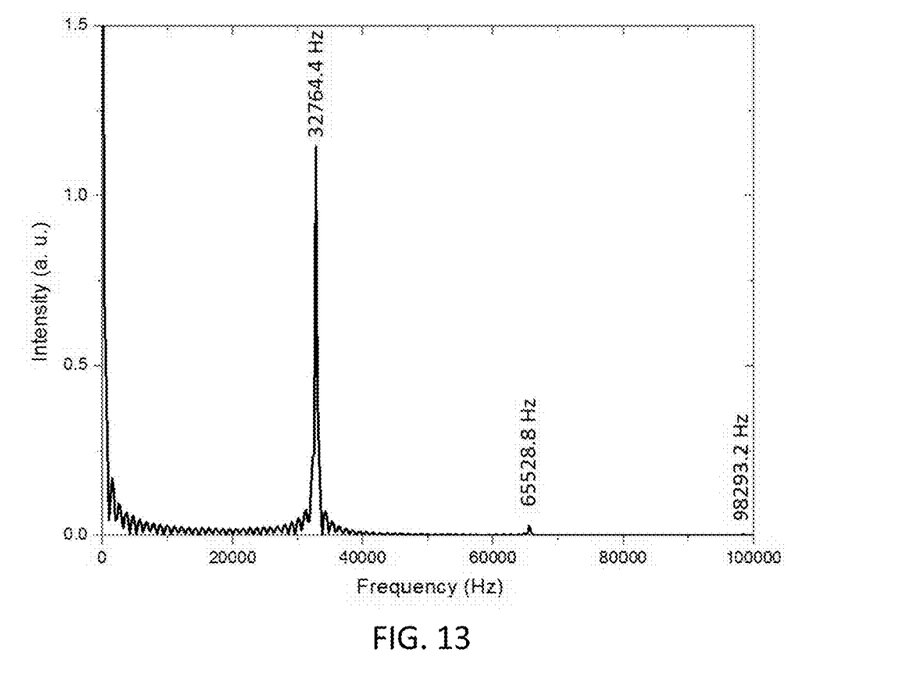
FIG. 13 shows the Fourier transform of the optimized sample absorption curve in FIG. 11 to reveal its frequency components.

FIG. 13 shows the frequency components of the optimized sample absorption curve in FIG. 12 after a Fourier transform of the signal. It shows that when the laser source is modulated by the customized waveform, the optimized absorption curve still contains the fundamental frequency component of 32764.4 Hz, however, the frequency components at the second harmonic frequency of 65528.8 Hz and the third harmonic frequency of 98293.2 Hz are much weaker compared to those in FIG. 11. Most important, the intensity of the fundamental frequency component is stronger than that in FIG. 11. This means when the laser source is modulated by the customized waveform, the energy radiated out from the sample has strong fundamental components and weak harmonic components. If the same sensor with only one resonant frequency as shown in FIG. 8 is used, the sensor can output larger signals. As a result, the customized modulation waveform produces stronger signal intensity at the sensor peak response frequency of 32764.4 Hz. The improved signal strength in sample radiated enemy at the sensor peak response frequency can benefit the detection sensitivity of the system.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

What is claimed is:

1. A system for measuring material concentration values in a sample, comprising:
    a plurality of laser sources modulated by their respective drivers at different frequencies, each laser source emits light into the sample;
    a signal generator to generate modulation waveforms provided to the drivers;
    a plurality of sensors to detect output signals from the sample;
    circuitry configured to combine the output signals detected by the plurality of sensors into a combined signal;

a data acquisition (DAQ) device to digitize the combined signal;

a processor configured to perform a Fourier transform on the digitized signal to obtain signal intensity at each of the modulation frequencies in parallel; and the processor is further configured to calculate the material concentration values in the sample.

2. The system of claim 1, wherein the plurality of laser sources are wavelength modulated or intensity modulated.

3. The system of claim 1, wherein the plurality of sensors have different resonant frequencies.

4. The system of claim 1, wherein the plurality of sensors are quartz tuning fork (QTF) sensors.

5. The system of claim 1, wherein the circuitry is a trans-impedance amplifier or a voltage adding circuit.

6. The system of claim 1, wherein the DAQ device digitizes the combined signal at a sampling rate that is at least the Nyquist sampling rate.

7. A method for measuring material concentration values in a sample, comprising:

directing light from a plurality of laser sources modulated by their respective drivers at different frequencies into the sample;

generating modulation waveforms provided to the drivers;

detecting output signals from the sample with a plurality of sensors;

combining and converting the output signals detected by the plurality of sensors into a voltage signal;

digitizing the combined voltage signal;

performing a Fourier transform on the digitized signal to obtain a signal intensity value corresponds to each sensor channel at each of the modulated frequencies in parallel; and calculating the material concentration values in the sample.

8. The method of claim 7, wherein the plurality of sensors have different resonant frequencies.

9. The method of claim 7, wherein the plurality of sensors are quartz tuning fork (QTF) detectors.

10. The method of claim 7, wherein the output signals are combined by a trans-impedance amplifier or a voltage adding circuit.

11. The method of claim 7, wherein the voltage signal is digitized at a sampling rate that is at least the Nyquist sampling rate.

12. The method of claim 7, wherein the modulation waveform generated by the signal generator is optimized to improve the signal intensity in the sensor output signals by:

generating a custom modulation waveform connected to the driver of the laser source;

transmitting the modulated light from the laser source through a reference cell and detecting a sample absorption curve of the reference cell;

measuring a sample absorption frequency spectrum;

measuring a sensor frequency response spectrum and identifying a sensor peak response frequency; and designing a customized modulation waveform to alter a wavelength modulation speed of the laser source , to improve the signal intensity at the sensor peak response frequency, in the sample absorption frequency spectrum.

13. The method of claim 12, wherein designing the customized modulation waveform comprising:

slowing down a laser wavelength modulation speed when a laser output wavelength is near the absorption peak wavelength of the sample.

14. The system of claim 1, wherein the wherein the signal generator is configured to optimize the modulation waveform generation to improve the signal intensity in the sensor output signals by:

generating a custom modulation waveform connected to the driver of the laser source;

transmitting the modulated light from the laser source through a reference cell and detecting a sample absorption curve of the reference cell;

measuring a sample absorption frequency spectrum;

measuring a sensor frequency response spectrum and identifying a sensor peak response frequency; and designing a customized modulation waveform to alter a wavelength modulation speed of the laser source, to improve the signal intensity at the sensor peak response frequency, in the sample absorption frequency spectrum.

15. The system of claim 14, wherein designing the customized modulation waveform comprising:

slowing down a laser wavelength modulation speed when a laser output wavelength is near the absorption peak wavelength of the sample.

\* \* \* \* \*